(12) United States Patent
Devic et al.

(10) Patent No.: US 8,912,370 B2
(45) Date of Patent: Dec. 16, 2014

(54) METHOD FOR PRODUCING HEXAFLUOROPROPANE

(75) Inventors: Michel Devic, Sainte Foy les Lyon (FR); Nicolas Doucet, Lyons (FR); Laurent Wendlinger, Soucieu en Jarrest (FR); Geraldine Cavallini, Saint-Symphorien d'Ozon (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 13/377,159

(22) PCT Filed: May 5, 2010

(86) PCT No.: PCT/FR2010/050859
§ 371 (c)(1),
(2), (4) Date: Jan. 10, 2012

(87) PCT Pub. No.: WO2010/142877
PCT Pub. Date: Dec. 16, 2010

(65) Prior Publication Data
US 2012/0101314 A1    Apr. 26, 2012

(30) Foreign Application Priority Data
Jun. 12, 2009 (FR) ..................... 09 53941

(51) Int. Cl.
*C07C 17/354* (2006.01)
*C07C 19/08* (2006.01)
*C07C 21/18* (2006.01)

(52) U.S. Cl.
CPC ............... *C07C 17/354* (2013.01); *C07C 21/18* (2013.01); *C07C 19/08* (2013.01)
USPC ........................................ 570/175

(58) Field of Classification Search
USPC .......................................... 570/175
See application file for complete search history.

(56) References Cited

U.S. PATENT DOCUMENTS

2009/0131727 A1* 5/2009 Yang et al. .................... 570/175

FOREIGN PATENT DOCUMENTS

| CN | 101148395 | 3/2008 |
| EP | 1916232 | 4/2008 |

OTHER PUBLICATIONS

Knunyants, I. L. et al. Reactions of Fluoro Olefins, Communication 13, Catalytic Hydrogenation of Perfluoro Olefins, No. 8, Aug. 1960, pp. 1312-1317.*
Knunyants, M.P., et al., Reactions of Fluoro Olefins, Journal of the USSR Academy of Sciences, Communication 13, Catalytic Hydrogenation of Perfluoro Olefins, No. 8, Aug. 1960, pp. 1412-1418, Chem Abstracts accession No. 1961:2127.

* cited by examiner

*Primary Examiner* — Jafar Parsa
*Assistant Examiner* — Medhanit Bahta
(74) *Attorney, Agent, or Firm* — Brinks Gilson & Lione

(57) ABSTRACT

The present invention relates to a method for producing 1,1,1,2,3,3-hexaafluoropropane, involving reacting gaseous phase hexafluoropropene with hydrogen in a superstoichiometric amount in the presence of a hydrogenation catalyst in a reactor, and recirculating a part of the gaseous effluent from the reactor.

12 Claims, No Drawings

METHOD FOR PRODUCING HEXAFLUOROPROPANE

FIELD OF THE INVENTION

The present invention relates to a process for the manufacture of 1,1,1,2,3,3-hexafluoropropane by hydrogenation of hexafluoropropene.

BACKGROUND OF THE INVENTION

The document by Knunyants et al., Journal of the USSR Academy of Sciences, Chemistry Department, "Reactions of fluoro-olefins", Report 13, "Catalytic hydrogenation of perfluoro-olefins", 1960, describes the substantially quantitative hydrogenation of hexafluoropropene (HFP) over a catalyst based on palladium supported on alumina, the temperature changing from 20° C. to 50° C. and then being maintained at this value.

1,1,1,2,3,3-Hexafluoropropane is of use in the manufacture of 1,2,3,3,3-pentafluoropropene.

The tests of the abovementioned prior art were carried out on the laboratory scale and the documents are entirely silent with regard to the lifetime of these catalysts.

The hydrogenation reaction as described above is highly exothermic and presents problems on the industrial scale. This high exothermicity is harmful to the lifetime of the catalyst.

The presence of a compound other than the reactants in the reaction stream can also be the cause of a rapid deactivation of the catalyst.

Furthermore, the document EP 1 916 232 provides a reaction for the multistage hydrogenation of an olefinic compound in order to obtain a high conversion and a high selectivity. Example 1 describes the reaction for the staged hydrogenation of hexafluoropropene in the presence of a catalyst supported on charcoal in four reactors with a temperature of the gas stream at the outlet of the first reactor of 66° C., a temperature of 104° C. at the outlet of the second reactor (for a conversion of 40%), a temperature of 173° C. at the outlet of the third reactor and a temperature of 100° C. at the outlet of the fourth reactor. Cooling stages are provided between the reactors with a temperature of the first bath of 55° C. and a temperature of the second bath of 111° C.

The process as described in the document EP 1 916 232 is expensive in terms of capital cost and, in addition, it is not easy to carry it out.

DETAILED DESCRIPTION OF THE INVENTION

The process according to the present invention makes it possible to control the exothermicity of the hydrogenation reaction while retaining a very good conversion and selectivity and/or to reduce the deactivation of the catalyst.

The process according to the present invention is characterized in that (i) hexafluoropropene is reacted in the gas phase with hydrogen in a superstoichiometric amount at a temperature of between 50 and 200° C., preferably of between 80 and 120° C., in the presence of a hydrogenation catalyst; (ii) a portion of the gaseous output stream resulting from the reactor, comprising 1,1,1,2,3,3-hexafluoropropane (HFC-236ea), unreacted hydrogen and optionally unreacted hexafluoropropene, 1,1,1,2,3-pentafluoropropane (HFC-245eb) and 1,1,1,2-tetrafluoropropane (HFC-254eb), is recycled and (iii) 1,1,1,2,3,3-hexafluoropropane is recovered from the other portion of the gaseous output stream resulting from the reactor, optionally after a purification stage.

Preferably, the temperature at the inlet of the reactor is between 30 and 100° C., advantageously between 40 and 80° C.

The gas stream comprising the recycling loop and the reactants can be preheated before introduction into the reactor.

The process according to the present invention is preferably carried out with a hydrogen/HFP molar ratio of between 1 and 50, advantageously of between 2 and 15.

The contact time, defined as the ratio of the volume of the catalytic bed to the flow rate by volume of the total stream under standard temperature and pressure conditions, is preferably between 0.1 and 20 s and advantageously between 0.5 and 5 s.

The hydrogenation reaction according to the present invention is preferably carried out at an absolute pressure of between 0.5 and 20 bar and advantageously of between 1 and 5 bar.

The gaseous output stream at the outlet of the reactor preferably comprises approximately from 2 to 99% by volume of 1,1,1,2,3,3-hexafluoropropane, from 0.2 to 98% by volume of hydrogen, from 0 to 10% of 1,1,1,2,3,3-hexafluoropropene, from 0 to 5% of 1,1,1,2,3-pentafluoropropane and from 0 to 1% of 1,1,1,2-tetrafluoropropane.

Advantageously, the gaseous output stream at the outlet of the reactor comprises from 50 to 98% by volume of 1,1,1,2,3,3-hexafluoropropane, from 2 to 50% by volume of hydrogen, from 0 to 0.1% of 1,1,1,2,3,3-hexafluoropropene, from 0 to 1% of 1,1,1,2,3-pentafluoropropane and from 0 to 0.5% of 1,1,1,2-tetrafluoropropane.

According to the process of the invention, an adiabatic reactor is preferably used.

The portion of the gaseous output stream recycled to the reactor preferably represents at least 90% by volume of the whole of the output stream at the outlet of the reactor, advantageously at least 93% by volume. Particularly preferably, the portion of the output stream recycled to the reactor represents between 94 and 98% by volume of the total output stream at the outlet of the reactor.

Mention may in particular be made, as catalyst, of those based on a metal from Group VIII or rhenium. The catalyst can be supported, for example on carbon, alumina, aluminium fluoride, and the like, or can be unsupported, such as Raney nickel. Use may be made, as metal, of platinum or palladium, in particular of palladium, advantageously supported on carbon or alumina. It is also possible to combine this metal with another metal, such as silver, copper, gold, tellurium, zinc, chromium, molybdenum and thallium.

Preferably, the catalyst comprises optionally supported palladium.

The catalyst very particularly preferred according to the present invention is a catalyst comprising palladium supported on alumina. The amount of palladium in the catalyst is preferably between 0.05 and 10% by weight and advantageously between 0.1 and 5%

The specific surface of the catalyst is preferably greater than 4 $m^2/g$ and the alumina used as catalytic support is advantageously provided in the α polymorphic form.

The Applicant Company has noticed, surprisingly, that the reactivity of 1,1,1,2,3,3-hexafluoropropane under the hydrogenation conditions of the present invention is very low. The process according to the present invention makes it possible to achieve an HFP conversion of greater than 99%, indeed even 99.5% and even greater than 99.8%, and an HFC-236ea selectivity of greater than 99%, indeed even 99.5% and even greater than 99.8%. In addition, these performances are stable over time.

EXPERIMENTAL PART

Example 1

Use is made of a tubular reactor made of stainless steel, with an internal diameter of 2.1 cm and a length of 120 cm, containing 479 g, i.e. 330 cm$^3$, of catalyst in the form of a fixed bed. The catalyst comprises 0.2% by weight of palladium supported on α-alumina.

Throughout the duration of the reaction, 1.05 mol/h of hydrogen and 0.7 mol/h of hexafluoropropene are continuously injected and the flow rate within the recycling loop is 0.480 Sm$^3$/h (representing a degree of recycling of 95.3% by volume). The pressure is 2 bar absolute. The hydrogen/HFP molar ratio at the inlet of the reactor is 11.6, the temperature at the reactor inlet is 31° C. and the maximum temperature achieved during the reaction is 121° C. The contact time is 2.28 s.

An HFP conversion of 100%, an HFC-236ea selectivity of 99.39%, an HFC-245eb selectivity of 0.53% and an HFC-254eb selectivity of 0.07% are obtained.

No deactivation was observed during 118 h of operation.

Example 2

The operation is carried out as in Example 1, except that the temperature at the inlet of the reactor is 81° C. and the maximum temperature achieved during the reaction is 157.8° C.

An HFP conversion of 100%, an HFC-236ea selectivity of 98.6%, an HFC-245eb selectivity of 1.26% and an HFC-254eb selectivity of 0.12% are obtained.

Example 3

Use is made of a tubular reactor made of stainless steel, with an internal diameter of 2.1 cm and a length of 120 cm, containing 479 g, i.e. 330 cm$^3$, of catalyst in the form of a fixed bed. The catalyst comprises 0.2% by weight of palladium supported on α-alumina.

Throughout the duration of the reaction, 0.84 mol/h of hydrogen and 0.7 mol/h of hexafluoropropene are continuously injected and the flow rate within the recycling loop is 0.480 Sm$^3$/h (representing a degree of recycling of 96.2% by volume). The pressure is 2 bar absolute. The hydrogen/HFP molar ratio at the inlet of the reactor is 6, the temperature at the reactor inlet is 46.7° C. and the maximum temperature achieved during the reaction is 121.4° C. The contact time is 2.31 s.

An HFP conversion of 100%, an HFC-236ea selectivity of 99.34%, an HFC-245eb selectivity of 0.60% and an HFC-254eb selectivity of 0.04% are obtained.

Example 4

The operation is carried out as in Example 3, except that 1.4 mol/h of hydrogen are injected continuously and the flow rate of the recycling loop is 93.9%. The hydrogen/HFP molar ratio at the inlet of the reactor is 17, the temperature at the inlet of the reactor is 45.8° C. and the maximum temperature achieved during the reaction is 134.3° C.

An HFP conversion of 100%, an HFC-236ea selectivity of 99.54%, an HFC-245eb selectivity of 0.39% and an HFC-254eb selectivity of 0.03% are obtained.

The invention claimed is:

1. A process for the manufacture of 1,1,1,2,3,3-hexafluoropropane, comprising (i) reacting hexafluoropropene in the gas phase with hydrogen in a superstoichiometric amount at a temperature of between 50 and 200° C., in the presence of a hydrogenation catalyst to produce a gaseous output stream, wherein the catalyst comprises supported palladium; (ii) recycling a first portion of the gaseous output stream from the reactor, comprising 1,1,1,2,3,3-hexafluoropropane, unreacted hydrogen and optionally unreacted hexafluoropropene, 1,1,1,2,3-pentafluoropropane and 1,1,1,2-tetrafluoropropane, and (iii) recovering 1,1,1,2,3,3-hexafluoropropane from a second portion of the gaseous output stream from the reactor, optionally after a purification stage, wherein the recycled, first portion of the gaseous output stream represents at least 90% by volume, of the output stream.

2. Process according to claim 1, characterized in that the gaseous output stream comprises from 2 to 99% by volume of 1,1,1,2,3,3-hexafluoropropane, from 0.2 to 98% by volume of hydrogen, from 0 to 10% by volume of hexafluoropropene, from 0 to 1% of 1,1,1,2-tetrafluoropropane and from 0 to 5% of 1,1,1,2,3-pentafluoropropane.

3. Process according to claim 1, characterized in that the support is based on alumina.

4. Process according to claim 1, characterized in that the hydrogen/hexafluoropropene molar ratio is between 1 and 50.

5. Process according to claim 1, characterized in that the contact time is between 0.1 and 20 s.

6. Process according to claim 1, characterized in that the reaction is carried out at a pressure of between 0.5 and 20 bar absolute.

7. Process according to claim 1, characterized in that the hydrogenation reaction is carried out continuously.

8. Process according to claim 1, characterized in that the temperature is between 80 and 120° C.

9. Process according to claim 1, characterized in that between 94 and 98% by volume of the output stream is recycled.

10. Process according to claim 1, characterized in that the hydrogen/hexafluoropropene molar ratio is between 2 and 15.

11. Process according to claim 1, characterized in that the reaction is carried out at a pressure of between 1 and 5 bar absolute.

12. Process according to claim 1, characterized in that the contact time is between 0.5 and 5 s.

* * * * *